(12) United States Patent
Fujii et al.

(10) Patent No.: US 10,835,764 B2
(45) Date of Patent: Nov. 17, 2020

(54) DOSE EVALUATION SYSTEM, PLANNING SYSTEM, PARTICLE IRRADIATION SYSTEM AND DOSE EVALUATION METHOD

(71) Applicants: HITACHI, LTD., Tokyo (JP); NATIONAL UNIVERSITY CORPORATION HOKKAIDO UNIVERSITY, Sapporo-shi, Hokkaido (JP)

(72) Inventors: Yusuke Fujii, Sapporo (JP); Taeko Matsuura, Sapporo (JP); Yuka Matsuzaki, Sapporo (JP); Kikuo Umegaki, Sapporo (JP); Hiroki Shirato, Sapporo (JP); Hidenori Koyano, Sapporo (JP); Takahiro Yamada, Tokyo (JP); Rintarou Fujimoto, Tokyo (JP)

(73) Assignees: HITACHI, LTD., Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 127 days.

(21) Appl. No.: 16/089,410

(22) PCT Filed: Mar. 23, 2017

(86) PCT No.: PCT/JP2017/011866
§ 371 (c)(1),
(2) Date: Sep. 28, 2018

(87) PCT Pub. No.: WO2017/170178
PCT Pub. Date: Oct. 5, 2017

(65) Prior Publication Data
US 2020/0054897 A1 Feb. 20, 2020

(30) Foreign Application Priority Data
Mar. 30, 2016 (JP) .................................. 2016-069463

(51) Int. Cl.
*A61N 5/10* (2006.01)
*A61B 6/03* (2006.01)
(Continued)

(52) U.S. Cl.
CPC ............ *A61N 5/1067* (2013.01); *A61B 6/032* (2013.01); *A61B 6/4085* (2013.01);
(Continued)

(58) Field of Classification Search
CPC ................ A61N 5/1067; A61N 5/1071; A61N 2005/1072; A61B 6/032; A61B 6/4085; G01T 1/2914
(Continued)

(56) References Cited

U.S. PATENT DOCUMENTS

2011/0044429 A1* 2/2011 Takahashi .............. A61N 5/103
378/65
2011/0087090 A1 4/2011 Boernert et al.
(Continued)

FOREIGN PATENT DOCUMENTS

JP 3053389 B1 6/2000
JP 2006-223425 A 8/2006
(Continued)

OTHER PUBLICATIONS

International Search Report of PCT/JP2017/011866 dated Jun. 27, 2018.
(Continued)

Primary Examiner — Nicole M Ippolito
(74) Attorney, Agent, or Firm — Mattingly & Malur, PC

(57) ABSTRACT

A function/process of recording marker position data and spot data is provided. The marker position data includes
(Continued)

position information of a marker 29 measured for tumor tracking irradiation and information on time of execution of X-ray imaging. The spot data includes information on time of irradiation of each spot, a delivered irradiation position, and a delivered irradiation amount. The marker position data and the spot data are synchronized based on the time information, and by using the marker position data and the spot data upon spot irradiation, a delivered dose distribution of proton irradiation is calculated. With this configuration, it is possible to take the influence of interplay effect into consideration, and it is possible to support to make more appropriate determination upon replanning of a treatment plan.

13 Claims, 7 Drawing Sheets

(51) Int. Cl.
*A61B 6/00* (2006.01)
*G01T 1/29* (2006.01)
(52) U.S. Cl.
CPC .......... *A61N 5/1071* (2013.01); *G01T 1/2914* (2013.01); *A61N 2005/1072* (2013.01)

(58) Field of Classification Search
USPC .......................................... 250/492.1, 492.3
See application file for complete search history.

(56) References Cited

U.S. PATENT DOCUMENTS

| | | |
|---|---|---|
| 2012/0150017 A1 | 6/2012 | Yamaya et al. |
| 2014/0336438 A1 | 11/2014 | Bharat et al. |
| 2015/0036793 A1 | 2/2015 | Umekawa et al. |

FOREIGN PATENT DOCUMENTS

| | | |
|---|---|---|
| JP | 2012-210232 A | 11/2012 |
| JP | 5224421 B | 7/2013 |
| JP | 2014-45302 A | 3/2014 |
| JP | 2015-500053 A | 1/2015 |
| JP | 2015-029793 A | 2/2015 |

OTHER PUBLICATIONS

International Preliminary Report on Patentability received in corresponding International Application No. PCT/JP2017/011866 dated Oct. 11, 2018.

* cited by examiner

FIG.2

| SPOT NUMBER | IRRADIATION TIME [ms] | X[mm] | Y[mm] | SPOT DOSE [MU] |
|---|---|---|---|---|
| 1 | 10010.0 | -10.1 | 0 | 0.01 |
| 2 | 10020.0 | -4.9 | 0 | 0.02 |
| 3 | 10030.0 | 0.1 | 0 | 0.01 |
| 4 | 10040.0 | 5.1 | 0 | 0.01 |
| 5 | 10050.0 | 9.9 | 0 | 0.02 |

| X-RAY IRRADIATION NUMBER | IRRADIATION TIME [ms] | X[mm] | Y[mm] | Z[mm] | GATE SIGNAL |
|---|---|---|---|---|---|
| 1 | 1033.3 | 2.9 | 1.1 | 0.5 | OFF |
| 2 | 1066.6 | 2.0 | 1.0 | 0.4 | OFF |
| 3 | 1100.0 | 1.1 | 1.1 | 0.6 | OFF |
| 4 | 1133.3 | 0.0 | 0.9 | 0.6 | ON |
| 5 | 1166.6 | 0.1 | 1.0 | 0.4 | ON |

DOSE EVALUATION SYSTEM, PLANNING SYSTEM, PARTICLE IRRADIATION SYSTEM AND DOSE EVALUATION METHOD

TECHNICAL FIELD

The present invention relates to a dose evaluation system, a planning system, a particle irradiation system, and a dose evaluation method, preferably used upon treatment by irradiating a particle beam to an affected part such as a tumor.

BACKGROUND ART

As an example of a tumor tracking irradiation apparatus capable of calculating the position of a tumor which moves in a trunk automatically in a short time, and ensuring substantially required accuracy independently of the absolute accuracy of a mechanical system, Patent Literature 1 describes a dynamic body tracking irradiation apparatus including: imaging apparatuses to perform image pickup on a tumor marker embedded near the tumor simultaneously from first and second directions to obtain first and second video images; an image input recognition processor to perform template matching by shade normalized cross-correlation method of applying a previously-registered tumor marker template image to the digitized first and second video images on actual time level at a predetermined frame rate, and calculate first and second two-dimensional coordinates of the tumor marker based on first and second image transformation matrices; a central processing unit to calculate three-dimensional coordinates of the tumor marker based on the calculated first and second two-dimensional coordinates; and an irradiation controller to control a treatment beam irradiation with a linac based on the calculated three-dimensional coordinates of the tumor maker.

Further, to enable simultaneous acquisition of functional information and form information by simultaneously measuring and imaging externally-accessible same open space with a PET (Positron Emission Tomography) device and an MRI (Magnetic Resonance Imaging) device, Patent Literature 2 describes a technique in a PET/MRI multifunction machine as a combination of a PET device and an MRI device. The machine has an open PET device in which at least a part of a PET object visual field is externally-accessible open space, and an open MRI device in which at least a part of an MRI object visual field is externally-accessible open space. The open space of the PET object visual field and the open space of the MRI object visual field at least partially overlap each other.

CITATION LIST

Patent Literature

Patent Literature 1: Japanese Patent No. 3053389
Patent Literature 2: Japanese Patent No. 5224421

SUMMARY OF INVENTION

Technical Problem

A method of irradiation of a radioactive ray such as a particle beam or an X-ray to a cancer patient or the like is known. The particle beam includes a proton beam, a carbon ion beam and the like. A radiation exposure system used for irradiation forms a dose distribution appropriate to the shape of a target such as a tumor in the patient's body fixed on a patient bed called couch.

In the radiation exposure system, as a dose distribution forming method, a scanning irradiation method of scanning a thin particle beam with a magnet to form a dose distribution is becoming widespread.

When the target such as a tumor moves by breathing or the like, it is difficult to accurately irradiate the particle beam. Accordingly, gated irradiation of irradiating the particle beam only when the target exists within a predetermined range (gate range) has been recently realized.

The above-described Patent Literature 1 describes a method called tumor tracking irradiation of performing gated irradiation based on the position of a marker embedded near an affected part. The marker used in the gated irradiation as described in the Patent Literature 1 is, e.g., a metal sphere having a diameter of about 2 mm.

A general particle beam treatment is continuously performed for several days or several weeks. In such period, when the shape of the tumor is remarkably changed, the pattern of the irradiated particle beam (position, volume and energy) may be changed. The change of the particle beam pattern is called replanning. The abovementioned Patent Literature 2 discloses a method of referring to a PET image and an MRI image upon determination of execution of replanning.

Note that in the above-described scanning irradiation method, the thin particle beam is irradiated while the particle beam is scanned with the magnet. Thus a thin dose distribution called spot is arrayed, to form a dose distribution corresponding to the target. However, in this irradiation method, as the spot is sequentially formed, when the target moves during the irradiation, the relative positional relationship between the spots is changed.

In the scanning irradiation method, when the positional relationship between the spots becomes different from the plan, a hot spot and a cold spot may occur in the integrated dose distribution. The influence on the dose distribution by target movement is called interplay effect.

In the publicly-known techniques described in the above Patent Literature and the like, it is not possible to take the actual result of interplay effect into consideration upon determination of execution of replanning.

The present invention has an object to provide a dose evaluation system, a planning system, a particle irradiation system, and a dose evaluation system, to enable consideration of the influence of interplay effect and to support execution of more appropriate determination upon replanning of a treatment plan.

Solution to Problem

To solve the above problem, for example, the configuration described in the claims is adopted.

The present invention includes plural solutions to the above problem. As an example, there are provided an irradiation amount measuring device that measures an irradiation amount of a particle beam irradiated to a target; an irradiation position measuring device that measures an irradiation position of the particle beam irradiated to the target; an irradiation time recorder that records irradiation time at which the particle beam is irradiated; a tracking object position measuring part that measures a position of a tracking object being irradiated with the particle beam; a tracking object time recorder that records tracking object time at which the position of the tracking object is measured; and a dose distribution calculator that synchronizes the position of the tracking object being irradiated with the particle beam with the irradiation amount and the irradiation position of the particle beam at that time, by synchronizing the irradiation time with the tracking object time, and calculates a delivered dose distribution of irradiation to the target.

Advantageous Effects of Invention

According to the present invention, it is possible to quickly provide information on a delivered dose distribution in consideration of interplay effect. Accordingly, it is possible to support execution of appropriate determination in replanning.

BRIEF DESCRIPTION OF DRAWINGS

FIG. 2 is a conceptual diagram showing spot data in which spot irradiation time is recorded.

FIG. 3 is a conceptual diagram showing marker position data in which X-ray irradiation time and target position are recorded.

FIG. 5 is a conceptual diagram showing a screen to display a delivered dose distribution or the like.

DESCRIPTION OF EMBODIMENTS

Figure 1:
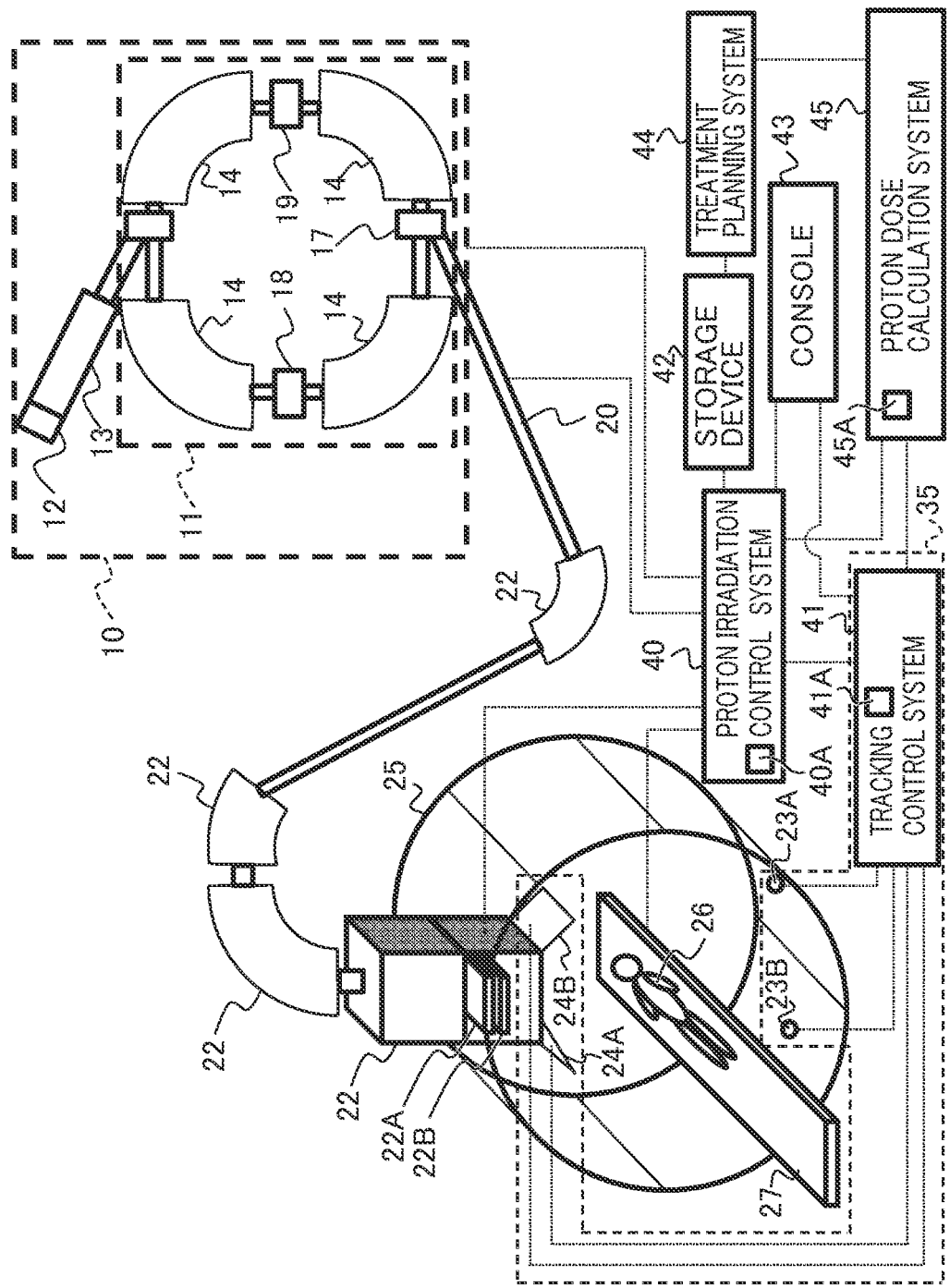
FIG. 1 is an entire configuration diagram showing a proton irradiation system according to an embodiment of the present invention.
Figure 4:
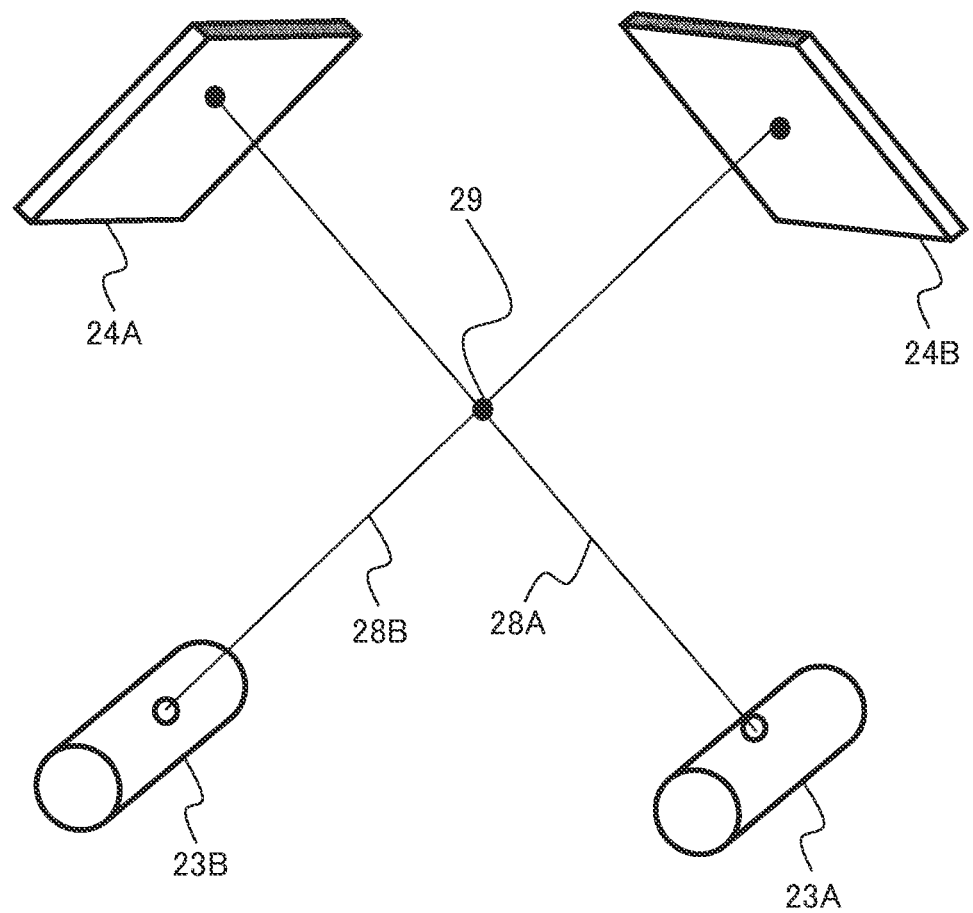
FIG. 4 is a conceptual diagram showing calculation of a marker position from a captured image with a tumor tracking apparatus.
Figure 5:
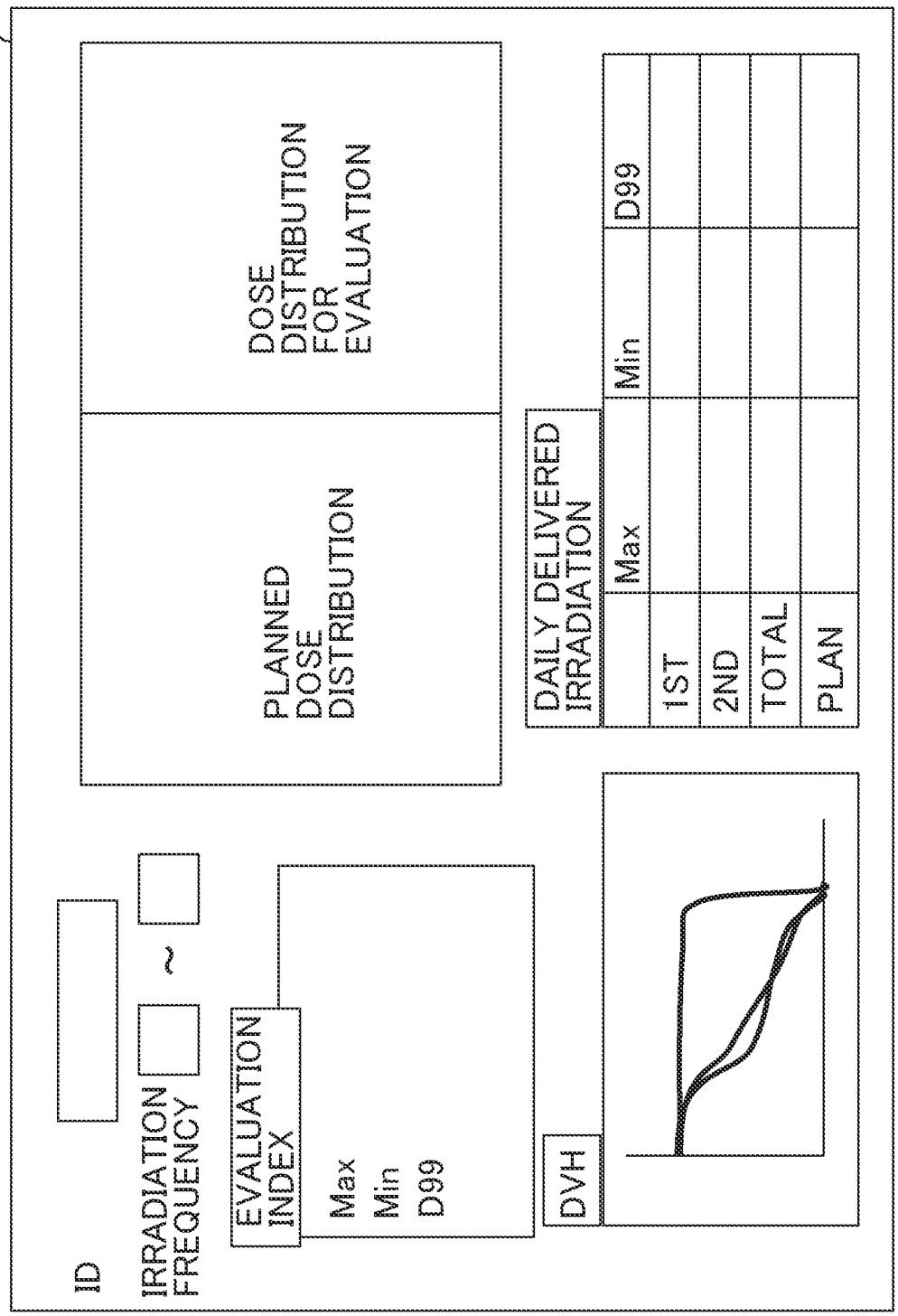
Figure 6:
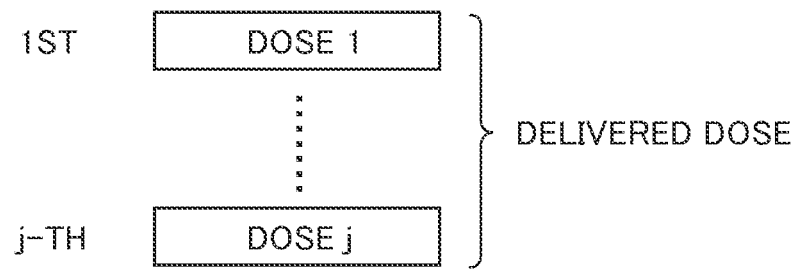
FIG. 6 is a conceptual diagram showing an optimized dose.
Figure 6:
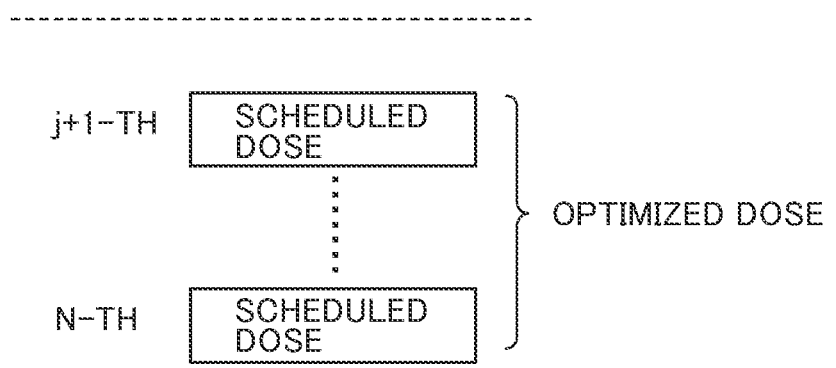
Figure 7:
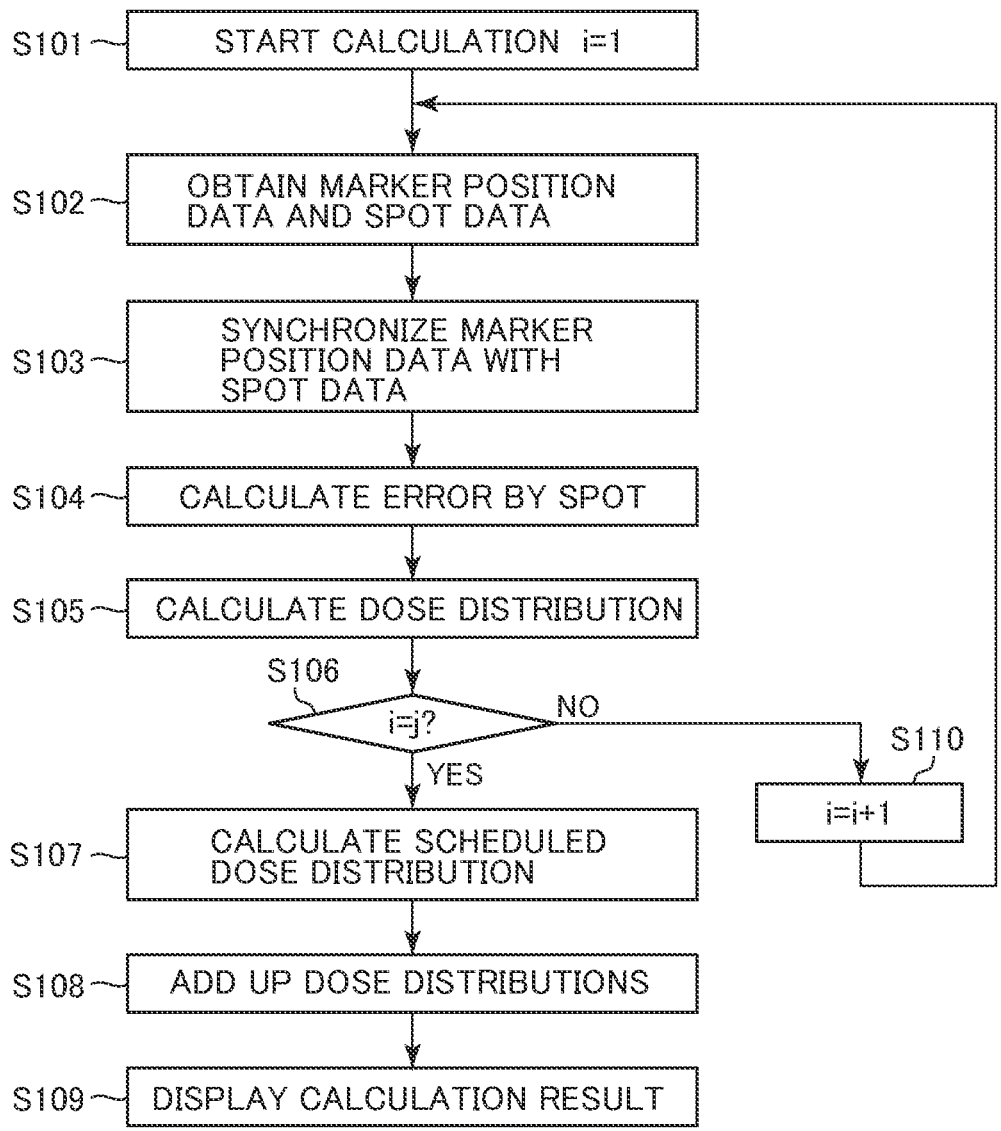
FIG. 7 is a flowchart showing a processing procedure of a proton dose evaluation system.

Embodiments of a dose evaluation system, a planning system, a particle irradiation system, and a dose evaluation method according to the present invention will be described using FIGS. 1 to 7. FIG. 1 is an entire configuration diagram showing the particle irradiation system. FIG. 2 is a conceptual diagram showing spot data in which spot irradiation time is recorded. FIG. 3 is a conceptual diagram showing marker position data in which X-ray irradiation time and target position are recorded. FIG. 4 is a conceptual diagram showing calculation of a marker position from a captured image with a tumor tracking apparatus. FIG. 5 is a conceptual diagram showing a screen to display a delivered dose distribution or the like. FIG. 6 is a conceptual diagram showing an optimized dose. FIG. 7 is a flow chart showing a processing procedure of a proton dose evaluation system.

The present invention is applicable to a particle irradiation system such as a proton irradiation system and a carbon ion beam irradiation system, a dose evaluation system such as a proton dose evaluation system or a carbon ion beam dose evaluation system, and a treatment planning system. In the present embodiment, using FIG. 1, a proton irradiation system and a proton dose evaluation system as examples will be described.

As shown in FIG. 1, the proton irradiation system as one of the embodiments of the present invention has a proton beam generator 10, a beam transport system 20, an irradiation nozzle 22, a tumor tracking apparatus 35, a couch 27, a proton irradiation control system 40, and a proton dose calculation system 45. A proton irradiation apparatus to irradiate a proton beam to a target has the proton beam generator 10, the beam transport system 20, and the irradiation nozzle 22.

The proton beam generator 10 has an ion source 12, a linac 13, and a synchrotron 11. The synchrotron 11 has a bending magnet 14, a quadrupole magnet (illustration omitted), an RF acceleration apparatus 18, an RF extraction apparatus 19, an extraction deflector 17 and the like. The ion source 12 is connected to the linac 13. The linac 13 is connected to the synchrotron 11. In the proton beam generator 10, the proton beam generated with the ion source 12 is pre-accelerated with the linac 13, and enters the synchrotron 11. The proton beam, further accelerated with the synchrotron 11, is extracted to the beam transport system 20.

The beam transport system 20 has plural bending magnets 21 and quadrupole magnets (illustration omitted). The beam transport system 20 is connected to the synchrotron 11 and an irradiation nozzle 22. Further, a part of the beam transport system 20 and the irradiation nozzle 22 are provided in a cylindrical rotating gantry 25, and are rotatable together with the rotating gantry 25. The proton beam extracted from the synchrotron 11, while passed through the inside of the beam transport system 20, is focused with the quadrupole magnet, the direction of which is changed with the bending magnets 21, and enters the irradiation nozzle 22.

The irradiation nozzle 22 has two pairs of scanning magnets, a dose monitor 22B, and a position monitor 22A. The two pairs of scanning magnets are provided in mutually orthogonal directions, to deflect the proton beam such that the proton beam arrives at a desired position in a plane vertical to the beam axis in the position of the target. The dose monitor 22B is a monitor to measure the irradiation amount of the proton beam irradiated to the target. The dose monitor 22B outputs the detected measurement value to the proton irradiation control system 40. The position monitor 22A is a monitor to indirectly measure the irradiation position of the proton beam irradiated to the target by detecting a position where the proton beam irradiated to the target has passed. The position monitor 22A outputs an obtained detection value to the proton irradiation control system 40. The proton beam passed through the irradiation nozzle 22 arrives at the target in the irradiation object 26. Note that when a patient having e.g. a cancer is treated, the irradiation object 26 represents the patient, and the target, a tumor or the like.

Abed on which the irradiation object 26 is placed is called couch 27. The couch 27 is movable in orthogonal three axial directions based on an instruction from the proton irradiation control system 40, and further, the couch 27 is rotatable about the respective axes. With these movement and rotation, the position of the irradiation object 26 is moved to a desired position.

The proton irradiation control system 40 is connected to the proton beam generator 10, the beam transport system. 20, the irradiation nozzle 22, a tracking control system 41, the couch 27, a storage device 42, a console 43, a proton dose calculation system 45 and the like. The proton irradiation control system 40 controls devices such as the proton beam generator 10, the beam transport system 20, and the irradiation nozzle 22. The proton irradiation control system 40 has an irradiation time recorder 40A which measures the irradiation amount of the proton beam with the dose monitor 22B, associates the irradiation amount with time upon measurement of the irradiation position of the proto beam with the position monitor 22A, and records them as spot data as shown in FIG. 2.

The tumor tracking apparatus 35 has two pairs of X-ray imaging apparatuses to obtain a captured image of a marker (tracking object) 29 in the irradiation object 26, an X-ray generator for imaging 23A and an X-ray imaging device 24A, an X-ray generator for imaging 23B and an X-ray imaging device 24B, and the tracking control system 41. The tracking object position measuring part is configured with the X-ray generators for imaging 23A and 23B to measure the position of the marker 29 being irradiated with the proton beam, and the X-ray imaging devices 24A and 24B.

The two sets of the X-ray generator for imaging 23A and the X-ray imaging device 24A, and the X-ray generator for imaging 23B and the X-ray imaging device 24B are provided such that the respective X-ray routes intersect each other. Note that it is preferable that the two pairs of X-ray generators for imagines 23A and 23B, and the X-ray imaging devices 24A and 24B are provided in mutually orthogonal directions, however, they may be provided in directions not orthogonal to each other. Further, the X-ray generators for imaging 23A and 23B and the X-ray imaging devices 24A and 24B are not necessarily provided inside the rotating gantry 25, but may be provided on a fixed place such as a ceiling or a floor.

The tracking control system 41 calculates the position of the marker 29 based on signals inputted from the X-ray imaging apparatuses, and further, based on the position of the marker 29, determines whether or not extraction of the proton beam is allowed, and transmits a signal indicating propriety of proton-beam irradiation to the proton irradiation control system 40. The tracking control system 41 has a tracking object time recorder 41A to record time of X-ray irradiation by X-ray imaging (tracking object time), and records the calculation result of the position of the marker 29 and the status of the gate signal, as marker position data as shown in FIG. 3.

More specifically, as shown in FIG. 4, the tracking control system 41 performs imaging on the marker 29 by irradiating the X-ray generated with the X-ray generator for imaging 23A to the marker 29, and measuring a two-dimensional dose distribution of the X-ray passed through the marker 29 with the X-ray imaging device 24A. The tracking control system 41 performs imaging on the marker 29 by irradiating the X-ray generated with the X-ray generator for imaging 23B to the marker 29, and measuring a two-dimensional dose distribution of the X-ray passed through the marker 29 with the X-ray imaging device 24B. The tracking control system 41 calculates a three-dimensional position of the marker 29 embedded in the irradiation object 26 from the obtained two captured images, obtains the position of the target based on the result, and determines whether or not the obtained position of the target is within a previously-designated gate range (irradiation allowance range). When it is determined that the position of the target is within the gate range, the tracking control system 41 transmits a gate-on signal to the proton irradiation control system 40, to allow extraction. On the other hand, when it is determined that the position of the target is not within the gate range, the tracking control system 41 transmits a gate-off signal not to allow irradiation. The proton irradiation control system 40 controls irradiation of the proton beam based on the gate-on signal and gate-off signal generated with the tracking control system 41.

The acquisition of captured image with the X-ray imaging apparatus is performed at fixed interval of, e.g., 30 Hz. The acquired captured image shows the marker 29 embedded in the body. The position of the marker 29 in the irradiation object 26 is specified by template matching with respect to a prepared template image of the marker 29. Since it takes much time for searching in the entire range of the captured image, the position of the marker 29 is searched only within a predetermined size of range from the position of the marker 29 in a previous captured image as a center.

FIG. 4 shows a line 28A connecting the position of the marker 29 on the X-ray imaging device 24A detected by template matching to the X-ray generator for imaging 23A, and a line 28B connecting the position of the marker 29 on the X-ray imaging device 24B to the X-ray generator for imaging 23B. The two lines 28A and 28B ideally intersect at one point, and the intersection is the position where the marker 29 exists. However, actually, due to the influence of the accuracy of template matching, installation error of the X-ray imaging apparatus, and the like, generally two lines 28A and 28B do not intersect but they are in twisted relationship. It is possible to draw a common perpendicular line in positions of the two lines 28A and 28B, in the twisted relationship, closest to each other. The common perpendicular line is called common perpendicular. Then a middle point of the common perpendicular is the position of the marker 29.

Returning to FIG. 1, the proton dose calculation system 45 has a synchronization function of specifying the position of the marker 29 upon irradiation of each spot, from the marker position data recorded with the tracking object time recorder 41A of the tracking control system 41 and the spot data recorded with the irradiation time recorder 40A of the proton irradiation control system 40. Further, the proton dose calculation system 45 has various functions, i.e., a dose distribution calculation function of calculating a dose distribution using the target position by spot synchronized with the synchronization function, a dose distribution integration function of integrating the dose distribution calculated by irradiation day, to calculate a delivered dose distribution, a scheduled dose distribution calculation function of calculating a scheduled dose distribution of irradiation to be performed thereafter based on irradiation parameters in a treatment plan generated with the treatment planning system 44 to be described later, a dose distribution for evaluation calculation function of calculating a dose distribution for evaluation obtained by adding the delivered dose distribution and the scheduled dose distribution, a feature value calculation function of calculating feature values of the calculated delivered dose distribution, the scheduled dose distribution, and the dose distribution for evaluation, and a dose display function of displaying a planned dose distribution used in generation of the treatment plan, the calculated respective dose distributions and their feature values on the display 45A.

With these functions, the proton dose calculation system 45 calculates a dose distribution in consideration of delivered irradiation, and displays information necessary for replanning on the display 45A and provides the information to the operator.

The screen displayed on the display 45A with the dose display function is e.g. a screen as shown in FIG. 5. In FIG. 5, both of the planned dose distribution upon generation of a treatment plan and the obtained dose distribution for evaluation are displayed. The feature values calculated with the feature value calculation function and displayed on the display 45A are e.g. maximum dose or minimum dose within a target, an value representing a dose volume histogram (DVH) of e.g. D99 indicating a dose value with respect to 99% volume, and the like. Further, ID to specify an irradiation object and information on irradiation frequency, necessary for these calculations, are also displayed on the screen as shown in FIG. 5, and it is possible to set them.

Note that the integration of the dose distribution in the dose distribution integration function, the scheduled dose distribution calculation function and the dose distribution for evaluation calculation function in the proton dose calculation system 45, may be realized by a method of simply calculating the sum of doses, or by a method of integration in consideration of biological effect with respect to the particle beam, and any one of the methods may be employed.

One method in consideration of biological effect is LQ model. The LQ model represents the simplest biological effect. In accordance with this model, a cell survival ratio is represented as $S=\exp(-(a \times d + b \times d \times d))$. After the completion of a series of irradiations, the survival ratio of a finally-remained cell is represented as a product of S. Note that "a" and "b" are constants or values depending on linear energy transfer, and they change depending on cell type. "d" is a day's transfer dose.

Further, in the present invention, as the delivered dose distribution is taken into consideration, the daily dose value varies. Accordingly, the daily survival ratio value S also varies. As the displayed dose distribution, it is possible to display a dose in a case where the total cell viabilities are equal and a proton beam for dose distribution formation is irradiated by the same amount every day. In this manner, by converting to the dose of a particle beam for dose distribution formation and displaying it, it is possible to provide intuitive information to the operator who is accustomed to irradiation of a particle beam for dose distribution formation.

In the proton irradiation system according to the above-described embodiment, an irradiation method called spot scanning method is employed. The spot scanning method is forming a dose distribution corresponding to the shape of a target by arraying dose distributions formed with a thin proton beam. The feature of the proton beam is that it advances while loses energy in the body, and immediately before it stops, the energy loss is the maximum. The shape of the dose distribution by the energy loss is called Bragg curve. It has a peak at the end of the range. The depth of the peak formation with the proton beam is adjustable by changing the proton beam energy. Further, the shape of the dose distribution in a direction vertical to the beam axis formed with the proton beam is approximately a Gaussian distribution. The position for formation of the dose distribution in the direction vertical to the beam axis is adjustable by scanning the proton beam with the scanning magnets. It is possible to forma dose distribution which is uniform over the entire target by combining energy change and scanning with the scanning magnets.

The treatment planning system 44 determines irradiation parameters for the proton beam irradiated to the target. The determined irradiation parameters include a gantry angle, energy, an irradiation position, and an irradiation amount by each spot. The treatment planning system 44 is capable of calculating a dose distribution when the proton beam is irradiated with arbitrary irradiation parameters. When the operator designates a dose to be irradiated to the target, the treatment planning system 44 optimizes the irradiation parameters for the proton beam necessary to forma dose distribution to cover the target with the designated dose. The treatment planning system 44 calculates a dose distribution when the irradiation is performed based on the irradiation parameters obtained as a result of optimization, and presents the dose distribution to the operator. The irradiation parameters are transmitted to the storage device 42, and stored in the storage device 42.

Further, based on the calculated delivered dose distribution, the treatment planning system 44 again performs optimization (replanning and correction) on the irradiation parameters for the proton beam in the remaining part of the irradiation plan.

In the second optimization, the difference between the obtained delivered dose distribution and the final desired planned dose distribution is defined as a new planned dose distribution, and the remaining irradiation amount is optimized. The optimized irradiation parameters are the energy of the proton beam, the irradiation position, and the irradiation amount.

More specifically, as shown in FIG. 6, the first to j-th dose distributions are calculated, and the delivered dose distribution is obtained, and further, the difference from the target planned dose distribution is obtained. In addition, the irradiation parameters are optimized such that the integrated dose of the (j+1)-th to N-th dose corresponds to the difference. Further, in this second optimization, as the difference, not a simple dose difference but biological effect is taken into consideration. In this case, it is desirable that the parameters for the remaining number of times of irradiation are optimized so as to attain the biological effect which is to be obtained when irradiation is performed in accordance with the initial plan.

Returning to FIG. 1, the storage device 42 holds the irradiation parameters for irradiation generated with the treatment planning system 44. The proton irradiation control system 40 receives necessary information from the storage device 42 prior to irradiation. Further, in the storage device 42, the time of irradiation, the proton beam arrival position converted from the measurement result from the position monitor 22A, and the spot dose corresponding to the irradiation amount measured with the dose monitor 22B, are recorded as spot data, by each spot irradiation. Further, the position of the marker 29 measured with the X-ray generators for imaging 23A and 23B and the X-ray imaging devices 24A and 24B, the position and time of the marker 29 at that time, are recorded as marker position data, and stored in the storage device 42.

The console 43 is connected to the proton irradiation control system 40 and the tracking control system 41. The console 43 displays information on the monitor based on signals obtained from the proton irradiation control system 40 and the tracking control system 41. Further, the console 43 receives an input from the operator who operates the proton irradiation system, and transmits various control signals to the proton irradiation control system 40 and the tracking control system 41.

The proton dose evaluation system has the above-described dose monitor 22B, the position monitor 22A, the irradiation time recorder 40A, the X-ray generators for imaging 23A and 23B, the X-ray imaging devices 24A and 24B, the tracking object time recorder 41A, and the proton dose calculation system 45 having the display 45A, and the storage device 42.

Next, a procedure of irradiation of the proton beam will be described.

First, the irradiation object 26 is fixed on the couch 27. Then the couch 27 is moved so as to move the irradiation object 26 to a previously-planned position. At this time, by performing imaging to obtain captured images using the X-ray imaging apparatuses, it is checked that the irradiation object 26 has moved to the previously-planned position.

When the operator presses an irradiation preparation button on the console 43, the proton irradiation control system 40 reads the irradiation parameters from the storage device 42. In accordance with the gantry angle described in the read irradiation parameters, the operator presses a gantry rotation button on the console 43, to rotate the rotating gantry 25.

After the rotation of the rotating gantry 25, the operator presses an X-ray imaging start button on the console 43, to start X-ray irradiation with the tracking control system 41, to start imaging. Further, by the depression of the X-ray imaging start button, an X-ray imaging start signal is transmitted to the proton irradiation control system 40.

After the start of the X-ray imaging, the operator selects a marker 29 to be tracked on the screen, thus starts tracking of the marker 29 on the respective captured images obtained with the X-ray imaging apparatuses. The tracking of the marker 29 is performed by using template matching. In the template matching, a position which best matches the pattern of the marker 29 image previously registered as a template image is searched for on the captured image. A position having a maximum matching score on the respective captured images is detected as the marker 29, and is tracked.

After the execution of the tracking of the marker 29 is checked, a gate start button is pressed. By the depression of the gate start button, when the position of the marker 29 is within the gate range, a gate-on signal is transmitted from the tracking control system 41 to the proton irradiation control system 40.

Note that the X-ray imaging with the X-ray imaging apparatuses is performed at e.g. 30 Hz. In the tracking control system 41, by obtained X-ray captured image, the imaging time, position coordinates of the marker 29 calculated by template matching, and the state of the gate signal are recorded as marker position data as shown in FIG. 3. In FIG. 3, one X-ray imaging corresponds to one-line data. Note that the time is recorded on the basis of the moment of the depression of the X-ray imaging start button.

When the operator presses the irradiation start button on the console 43, the proton irradiation control system 40 accelerates the proton beam to energy for the initial irradiation, based on the information on the energy, the irradiation position and the irradiation amount read from the storage device 42.

More specifically, the proton irradiation control system 40 controls the ion source 12 and the linac 13, to pre-accelerate the proton beam generated with the ion source 12 with the linac 13, and inject the beam into the synchrotron 11.

Next, the proton irradiation control system 40 controls the synchrotron 11, to accelerate the injected proton beam to the energy for the initial irradiation. The proton beam circulated in the synchrotron 11 is accelerated with a radio frequency wave from the RF acceleration apparatus 18. The proton irradiation control system 40 controls the amount of excitation with the bending magnets 21 and the quadrupole magnets in the beam transport system. 20 such that the proton beam having the energy for the initial irradiation arrives at the irradiation nozzle 22 from the synchrotron 11. Further, the proton irradiation control system 40 sets the amount of excitation with the two scanning magnets in the irradiation nozzle 22 such that the proton beam arrives at the spot position for the initial irradiation in the irradiation parameters from the storage device 42.

After the completion of these settings, when the proton irradiation control system 40 has received the gate-on signal from the tracking control system 41, irradiation of the proton beam is started. Further, when the gate-off signal has been received, the proton irradiation control system 40 waits for reception of the gate-on signal.

After the reception of the gate-on signal, the proton irradiation control system 40 applies a radio frequency wave to the RF extraction apparatus 19, to start extraction of the proton beam. When the radio frequency wave is applied to the RF extraction apparatus 19, a part of the proton beam circulated in the synchrotron 11 is passed through the extraction deflector 17, then passed through the beam transport system 20, and arrives at the irradiation nozzle 22. The proton beam arrived at the irradiation nozzle 22 is scanned with the two scanning magnets, and is passed through the dose monitor 22B and the position monitor 22A, arrives at the target in the irradiation object 26, to form a dose distribution.

The irradiation amount by spot is registered as an irradiation parameter obtained from the storage device 42. When the irradiation amount measured with the dose monitor 22B becomes the registered value, the proton irradiation control system 40 controls the radio frequency wave for extraction, to stop the extraction of the proton beam.

After the extraction of the proton beam, the proton irradiation control system 40 calculates a proton beam arrival position in the target position from the position information of the proton beam measured with the position monitor 22A, and checks that the calculated position corresponds to the position registered as the irradiation parameter.

Further, after the extraction of the proton beam, the proton irradiation control system 40 records the time of irradiation of the proton beam, the irradiation position, and the irradiation amount, as shown in FIG. 2, as spot data. The time of irradiation of the proton beam is the time of application of the radio frequency wave to the extraction radio frequency wave on the basis of the time of reception of the X-ray imaging start signal with the proton irradiation control system 40 from the tracking control system 41. The irradiation position is a value obtained by converting the position information of the proton beam measured with the position monitor 22A to the proton beam arrival position in the target position. The irradiation amount is a value of the spot dose obtained from the value measured with the dose monitor 22B. The data for one spot corresponds to one line in FIG. 2.

To irradiate the next spot, the proton irradiation control system 40 sets the amount of excitation with the two scanning magnets such that the proton beam arrives at the position registered as the irradiation parameter. After the setting, when the gate-on signal is continuously received, the proton irradiation control system 40 controls the radio frequency wave for extraction, to start extraction of the proton beam. When the gate-off signal has been received, the proton irradiation control system. 40 waits for reception of the gate-on signal. When the gate-off signal is received in the middle of irradiation of one spot, the extraction of the proton beam is continued by the completion of the irradiation of the spot.

The irradiation of spot is repeated, and when all the spots have been irradiated with irradiation with the initial energy, the proton irradiation control system 40 controls the synchrotron 11 to decelerate the proton beam, thus starts preparation for irradiation of the proton beam with the next energy. As in the case of the initial energy, the proton irradiation control system 40 controls the ion source 12 and the linac 13 to inject the proton beam to the synchrotron 11, then controls the synchrotron 11 to accelerate the proton beam to the second energy. The proton irradiation control system 40 controls the beam transport system 20 and the two scanning magnets to continue the spot irradiation, and records the position information of the proton beam measured with the position monitor 22A, the irradiation amount measured with the dose monitor 22B, and the time of irradiation.

The above-described operation is repeated, to irradiate all the spots read from the storage device 42. When the irradiation is completed, the proton irradiation control system 40 transmits an irradiation completion signal to the tracking control system 41. The tracking control system 41 receives the irradiation completion signal, then controls the X-ray generators for imaging 23A and 23B, to stop the X-ray imaging.

When the target is irradiated from plural directions, the angle of the rotating gantry 25 and the position of the couch 27 are changed, then the operator presses the irradiation preparation button, thus similarly repeats the irradiation of the proton beam.

When all the irradiation has been completed, the marker position data generated with the tracking control system 41 and the spot data generated with the proton irradiation control system 40 are outputted to the storage device 42 and stored there.

The above-described irradiation process is repeatedly performed once a day, for N days.

Next, using FIG. 7, a procedure when the proton dose calculation system 45 obtains a dose distribution for evaluation from a delivered dose distribution and displays the obtained dose distribution on the display 45A, for determination of replanning, will be described. In the present embodiment, the number of all the irradiation times of proton beam is N times, and the irradiation to the j-th time has been completed.

The proton dose calculation system 45 respectively calculates dose distributions in the i=1st to i=j-th irradiations, based on the marker position data and the spot data. The proton dose calculation system 45 calculates dose distributions in the i=j+1 to i=N-th irradiations as predictive values. Then proton dose calculation system 45 integrates the dose distributions in the i=1st to i=N-th irradiations, and displays the result of integration.

More specifically, first, at step S101 shown in FIG. 7, the proton dose calculation system 45 starts calculation from the i=1st irradiation.

Next, at step S102, the proton dose calculation system 45 obtains the marker position data and the spot data from the storage device 42.

Next, at step S103, the proton dose calculation system 45 synchronizes the marker position data with the spot data obtained from the storage device 42, with the synchronization function of the proton dose calculation system 45. More specifically, as the times recorded in the respective data are on the basis of the timing of depression of the X-ray imaging start button, it is possible to synchronize the times with each other. Accordingly, based on the recorded time, the position of the marker 29 at the moment of the irradiation of each spot is obtained. When the X-ray imaging is performed at 30 Hz, the marker position data is recorded by 33 ms. The marker 29 position at the moment of irradiation of each spot may be marker position data having the closest time or may be data interpolated from two marker position data having previous and subsequent times.

Next, at step S104, the proton dose calculation system 45 calculates the irradiation position in consideration of error.

More specifically, the proton dose calculation system 45 calculates the dose distribution in consideration of the influence of the motion of the target as a positional error of the spot. First, the target position upon spot irradiation calculated at the previous step S103 is projected to a plane including the isocenter vertical to the beam axis of the proton beam which differs at the angle of the rotating gantry 25, and the X-direction and Y-direction coordinates in the plane are obtained. Note that the X-direction and the Y-direction correspond to the directions of the respective scannings with the two pairs of scanning magnets. For example, in the case of the X-direction, when the target is moved in the X-direction by L, it is regarded that the position of the proton beam is moved in the X-direction by −L, and the dose distribution is calculated. At this time, as the influence of the non-rigid movement of the target in the body is small in the case of gated irradiation, it is regarded that such influence does not exist and the influence is ignored. In this manner, by taking the movement of the target into consideration, it is possible to calculate a dose distribution in consideration of movement of the target by using one CT image. Further, as described above, the spatial position of irradiation of the proton beam is recorded as spot data by spot. Accordingly, assuming that the X-coordinate of the spot recorded in the spot data is Xs, the irradiation position for dose calculation is set with the X-coordinate of the spot as Xs-L. Regarding the Y-direction, similar processing is repeated. Regarding the depth direction, calculation is performed by using the set value of the proton beam energy stored in the treatment planning system 44. Further, the irradiation amount for dose calculation is a value recorded in the spot data.

Next, at step S105, the proton dose calculation system 45 calculates the dose distribution by using the irradiation position for dose calculation and the irradiation amount for dose calculation obtained at the previous step S104, with the dose distribution calculation function of the proton dose calculation system 45. When the irradiation is performed at plural gantry angles, the dose distributions for all the gantry angles are calculated.

Next, at step S106, the proton dose calculation system 45 determines whether or not the calculation of the dose distribution to the j-th irradiation has been completed. When it is determined that the calculation has been completed, the process proceeds to step S107, while when it is determined that there is remaining of the calculation, the process returns via step S110 to step S102, to perform the calculation of the dose distribution for the next irradiation time.

Generally, upon generation of an irradiation plan, evaluation of dose distribution is performed on not a dose distribution per day but a finally-obtained integrated dose distribution. The present invention is a system preferably used in adaptive particle beam therapy to evaluate a dose distribution in the middle of a series of irradiation and perform replanning. Even when all the irradiation-completed dose distributions are integrated to obtain the delivered dose distribution, it is not the finally-obtained dose distribution. Accordingly, since it is more easily possible to determine whether or not a desired dose distribution is obtained by predicting irradiation-uncompleted dose distributions and adding them, it is desired to calculate dose distributions scheduled from the treatment plan.

Accordingly, at step S107, the proton dose calculation system 45 calculates predictive dose distributions in the j+1-th to N-th irradiations. The predictive dose distribution may be a dose distribution upon planning or may be an integrated delivered distribution normalized to an amount per day. It is possible to perform calculation on the assumption that the dose distributions in the j+1-th to N-th time irradiations are the same.

Next, at step S108, the proton dose calculation system 45 adds up the dose distributions to the j-th irradiation obtained at the previous steps S102 to S106 to generate the delivered dose distribution, with the dose distribution integration function of the proton dose calculation system 45. Further, the proton dose calculation system 45 adds the obtained delivered dose distribution to the predictive dose distributions, to generate a dose distribution for evaluation.

Next, at step S109, the proton dose calculation system 45 obtains a feature value of the obtained dose distribution for evaluation, with the dose display function of the proton dose calculation system 45. The proton dose calculation system 45 displays the dose distribution for evaluation and the feature value, together with the planned dose distribution and the like, as a screen as shown in FIG. 5, on the display 45A.

The operator checks the dose distribution for evaluation and the feature value displayed on the display 45A. The operator determines whether or not the irradiation to the present has been performed according to the plan, and determines whether or not replanning is required.

When the operator determines that replanning is required, the operator instructs recalculation by using an input unit of the console 43 (illustration omitted), an input unit of the treatment planning system 44 (illustration omitted), and an input unit of the proton dose calculation system 45 (illustration omitted).

When the recalculation is instructed, the treatment planning system 44 receives the data of the delivered dose distribution from the proton dose calculation system 45, to perform readjustment of the treatment plan to obtain a desired dose distribution.

Next, the effects of the present embodiment will be described.

The above-described dose evaluation system, the planning system, the particle irradiation system, and the dose evaluation method have a function/process of recording marker position data and spot data. The marker position data includes position information of the marker 29 measured for tumor tracking irradiation and information on time of execution of X-ray imaging. The spot data includes information on time of irradiation of each spot, a delivered irradiation position, and a delivered irradiation amount. The delivered dose distribution upon proton beam irradiation is calculated by synchronizing the marker position data and the spot data based on the time information and using the marker position data and the spot data upon spot irradiation.

According to this present embodiment, it is possible to consider whether or not replanning is to be performed and the details of the replanning, based on the delivered dose distribution in which information during the irradiation is projected. That is, it is possible to make determination of replanning in consideration of the influence of the interplay effect. Thus it is possible to make more appropriate determination in comparison with that in conventional art.

Further, upon calculation of delivered dose distribution, the proton dose calculation system 45 calculates the delivered dose distribution in consideration of biological effect. Thus it is possible to calculate a dose distribution in which the actual result of irradiation is more accurately projected, and it is possible to support execution of more appropriate determination.

Further, the proton dose calculation system 45 calculates a scheduled dose distribution of irradiation scheduled in the treatment plan. Thus it is more easily possible to determine whether or not a planned desired dose distribution is obtained, and it is possible to make more appropriate determination.

Further, the proton dose calculation system 45 has the display 45A to display at least one of the delivered dose distribution, the scheduled dose distribution, or the dose distribution for evaluation obtained by adding the delivered dose distribution and the scheduled dose distribution. Thus as it is possible to make determination based on visual sensation, it is possible to more accurately make determination.

Further, the proton dose calculation system 45 obtains a feature value of the dose distribution from the dose distribution for evaluation, and also displays the feature value on the display 45A. Thus it is possible to present more determination information upon determination of replanning, and it is possible to contribute to more appropriate determination.

Further, the treatment planning system. 44, provided with the dose evaluation system, generates a proton treatment plan. The proton dose calculation system 45 outputs the calculated delivered dose distribution to the treatment planning system 44. The treatment planning system 44 corrects the proton treatment plan based on the input delivered dose distribution so as to obtain a desired dose distribution. Thus it is possible to obtain a new planned dose distribution in consideration of the influence of interplay effect, and it is possible to perform more effective proton irradiation.

Further, the particle irradiation system further has the tracking control system 41 which determines whether or not the position of the target is within a previously designated range based on the position of the marker 29 measured with the X-ray generators for imaging 23A and 23B and the X-ray imaging devices 24A and 24B. When the tracking control system 41 determines that the position of the target is within the range, the tracking control system 41 outputs a signal to allow extraction of the proton beam to the proton irradiation control system 40. The proton irradiation control system 40 controls the proton beam based on the signal generated with the tracking control system 41. Thus it is possible to further improve the irradiation accuracy of the proton beam to the moving target, and it is possible to further improve the effect of proton irradiation.

Note that the present invention is not limited to the above-described embodiment, but various modifications and applications can be made. The above-described embodiment has been described in detail for explaining the present invention, and the invention is not necessarily limited to an embodiment having all the described constituent elements.

For example, the above-described embodiment has been described on the premise that the integration of dose distributions and the determination of the gated irradiation are performed only using X-ray CT images for planning obtained prior to the series of irradiation. However, it is possible to perform the integration of the dose distributions and the determination of the gated irradiation by appropriately using X-ray cone beam CT images (CBCT images) or X-ray CT images obtained in the middle of proton irradiation for treatment.

With the configuration of the proton irradiation system in the above-described embodiment, it is possible to obtain X-ray CBCT images by obtaining an X-ray captured images while rotating the rotating gantry 25. Such imaging can be performed immediately before or immediately after irradiation. Accordingly, it is possible to obtain a CT image closest to the status of the target upon irradiation. To calculate a dose distribution, a pixel value of the CT image called CT value is important since it relates to composition of matter. It is known that in the CBCT image, due to the limitation of its configuration, the accuracy of the CT value is lower than that of a general CT image. Accordingly, by performing transformation called non-rigid registration on the X-ray CT image for planning in accordance with the CBCT image, it is possible to calculate a dose distribution with higher accuracy, and it is possible to more appropriately make determination of replanning.

Further, in this case, the result of calculation of the dose distribution is obtained in accordance with the system of the CBCT. Since the number of dose distributions to be finally displayed must be one, it is desirable to perform transformation again by non-rigid registration in accordance with the system of X-ray CT image for planning.

Further, in the above-described embodiment, as a method of synchronization between the marker position data and the spot data, synchronization is performed by, on the basis of the moment of depression of the X-ray imaging start button, transmitting the X-ray imaging start signal from the tracking control system 41 to the proton irradiation control system 40. However, synchronization may be performed by using other methods. For example, at the moment of the completion of gantry rotation, the rotating gantry 25 transmits the rotation completion signal, in place of the X-ray imaging start signal, to the tracking control system 41 and the proton irradiation control system 40, and the synchronization is performed on the basis of the moment. Thus, other timings and signals may be used as a reference. Further, it may be configured such that a time recording device is provided outside, to receive signals about timings of recording from the tracking control system 41 and the proton irradiation control system 40, and perform recording.

Further, in the above-described embodiment, the tracking control system 41 is provided with the tracking object time recorder 41A, and the proton irradiation control system 40 is provided with the irradiation time recorder 40A. These respective time recorders may be provided in the proton dose calculation system 45.

Further, in the above-described embodiment, the respective calculation functions in the dose evaluation system are provided in the proton dose calculation system 45, and the functions are independent of the treatment planning system 44. The respective calculation functions of the dose evaluation system may be integrated with the treatment planning system 44. For example, a treatment planning system having the respective calculation functions of the proton dose evaluation system described in the present embodiment may be used as the dose evaluation system.

Further, the synchrotron has been described as an example of the accelerator to accelerate the proton beam; however, a cyclotron may be used as the accelerator.

Further, the irradiation method may be tracking irradiation of tracking an irradiation position based on the position of the marker 29 or the like, in place of gated irradiation. For example, in the X-ray chasing irradiation, the direction of the X-ray generator for distribution formation is changed in accordance with movement of the target, and the irradiation position of the X-ray is changed in accordance with movement of the target. In the case of the particle beam, it is possible to perform tracking irradiation by adjusting the amount of excitation with the scanning magnets in accordance with position of the target.

Further, the present invention is similarly applicable to the raster scanning method and the line scanning method of irradiating a thin particle beam without stopping the particle beam in addition to the spot scanning method described in the above embodiment.

Further, the evaluated particle beam is not limited to the proton beam. The present invention is similarly applicable to a heavy particle beam such as a carbon ion beam.

Further, in the above-described embodiment, the tracking object is the marker 29, and the position of the marker 29 is used as the marker position data. It may be configured such that the tracking object is the target itself, and the position of the target is used as the data. Further, the tracking object may be an object other than the target which moves in conjunction with the movement of the target. The other tracking object may be a bone as a high density region such as a rib bone in the irradiation object 26. The position of such object may be used as the position data.

LIST OF REFERENCE SIGNS

10 . . . proton beam generator
11 . . . synchrotron
12 . . . ion source
13 . . . linac
14 . . . bending magnet
17 . . . extraction deflector
18 . . . RF acceleration apparatus
19 . . . RF extraction apparatus
20 . . . beam transport system
21 . . . bending magnet
22 . . . irradiation nozzle
22A . . . position monitor
22B . . . dose monitor
23A, 23B . . . X-ray generator for imaging
24A and 24B . . . x-ray imaging device
25 . . . rotating gantry
26 . . . irradiation object
27 . . . couch
28A, 28B . . . line
29 . . . marker
35 . . . tumor tracking apparatus
40 . . . proton irradiation control system
40A . . . irradiation time recorder
41 . . . tracking control system
41A . . . tracking object time recorder
42 . . . storage device
43 . . . console
44 . . . treatment planning system
45 . . . proton dose calculation system
45A . . . display

The invention claimed is:

1. A dose evaluation system comprising:
an irradiation amount measuring device that measures an irradiation amount of a particle beam irradiated to a target;
an irradiation position measuring device that measures an irradiation position of the particle beam irradiated to the target;
an irradiation time recorder that records irradiation time at which the particle beam is irradiated;
a tracking object position measuring part that measures a position of a tracking object being irradiated with the particle beam;
a tracking object time recorder that records tracking object time at which the position of the tracking object is measured; and
a dose distribution calculator that synchronizes the position of the tracking object being irradiated with the particle beam with the irradiation amount and the irradiation position of the particle beam at that time, by synchronizing the irradiation time with the tracking object time, and calculates a delivered dose distribution of irradiation to the target, wherein the delivered dose distribution is obtained by integration of dose distributions in the first to J-th ($1 \leq J \leq N-1$) irradiations when the particle beam is irradiated to the tracking object dividedly N times (N=1, 2, ..., N), and wherein the dose distribution calculator calculates a scheduled dose distribution of irradiation scheduled in the J+1-th to N-th irradiations, and adds the delivered dose distribution and the scheduled dose distribution, to obtain a dose distribution for evaluation.

2. The dose evaluation system according to claim 1, wherein the dose distribution calculator uses X-ray CBCT images obtained with the tracking object position measuring part before and after irradiation of the particle beam, or CT images for planning transformed in accordance with the X-ray CBCT images, as X-ray CT images used for specifying the position of the target upon calculation of the delivered dose distribution.

3. The dose evaluation system according to claim 1, wherein, upon calculation of the delivered dose distribution, the dose distribution calculator calculates the delivered dose distribution in consideration of biological effect.

4. The dose evaluation system according to claim 1, wherein the dose distribution calculator calculates the scheduled dose distribution of irradiation scheduled in an irradiation plan.

5. The dose evaluation system according to claim 4, wherein the dose distribution calculator has a display to display at least one of the delivered dose distribution, the scheduled dose distribution, or a dose distribution for evaluation obtained by adding the delivered dose distribution and the scheduled dose distribution.

6. The dose evaluation system according to claim 5, wherein the dose distribution calculator obtains a feature value of the dose distribution from the dose distribution for evaluation, and also displays the feature value on the display.

7. The dose evaluation system according to claim 1, further comprising a storage device that holds the irradiation amount measured with the irradiation amount measuring device, the irradiation position measured with the irradiation position measuring device, the irradiation time recorded with the irradiation time recorder, the position of the tracking object measured with the tracking object position measuring part, and the tracking object time recorded with the tracking object time recorder.

8. The dose evaluation system according to claim 1, wherein the scheduled dose distribution is obtained from one of data normalized from a dose distribution per irradiation in the dose distribution in an irradiation plan or the delivered dose distribution.

9. A planning system having the dose evaluation system according to claim 1, for generating an irradiation plan using the particle beam, wherein the dose distribution calculator outputs the calculated delivered dose distribution to the planning system, and wherein the planning system corrects the irradiation plan using the particle beam based on the input delivered dose distribution so as to obtain a desired dose distribution.

10. A particle irradiation system comprising:
a particle irradiation apparatus to irradiate a particle beam to a target;
an irradiation control system that controls the particle irradiation apparatus; and
the dose evaluation system according to claim 1.

11. The particle irradiation system according to claim 10, further comprising a tracking control system that determines whether or not the position of the target is within a previously designated range based on the position of the tracking object measured with the tracking object position measuring part, and when it is determined that the position of the target is within the range, outputs a signal to allow extraction of the particle beam to the irradiation control system, wherein the irradiation control system controls the particle beam based on the signal generated with the tracking control system.

12. A dose evaluation method for calculation of a dose distribution of a particle beam irradiated to a target, comprising:

an irradiation amount measuring step of measuring an irradiation amount of the particle beam irradiated to the target;

an irradiation position measuring step of measuring an irradiation position of the particle beam irradiated to the target;

an irradiation time recording step of recording irradiation time at which the particle beam is irradiated;

a tracking object position measuring step of measuring a position of a tracking object being irradiated with the particle beam;

a tracking object time recording step of recording tracking object time at which the position of the tracking object is measured; and a dose distribution calculation step of synchronizing the position of the tracking object being irradiated with the particle beam with the irradiation amount and the irradiation position of the particle beam at that time, by synchronizing the irradiation time with the tracking object time, and calculating a delivered dose distribution of irradiation to the target, wherein the delivered dose distribution is obtained by integration of dose distributions in the first to J-th ($1 \leq J \leq N-1$) irradiations when the particle beam is irradiated to the tracking object dividedly N times (N= 1, 2, ..., N), and wherein the dose distribution calculation step calculates a scheduled dose distribution of irradiation scheduled in the J+1-th to N-th irradiations, and adds the delivered dose distribution and the scheduled dose distribution, to obtain a dose distribution for evaluation.

13. The dose evaluation method according to claim 12, wherein the scheduled dose distribution is obtained from one of data normalized from a dose distribution per irradiation in the dose distribution in an irradiation plan or the delivered dose distribution.

* * * * *